(12) United States Patent
Feustel et al.

(10) Patent No.: US 9,029,160 B2
(45) Date of Patent: May 12, 2015

(54) METHOD FOR DETERMINING THE CONTENT OF HYDROGEN SULFIDE IN CRUDE AND RESIDUAL OILS

(75) Inventors: Michael Feustel, Koengernheim (DE); Michael Brauchle, Bad Kreuznach (DE); Dominko Andrin, Schwalbach am Taunus (DE); Matthias Krull, Harxheim (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 14/001,325

(22) PCT Filed: Feb. 14, 2012

(86) PCT No.: PCT/EP2012/000651
§ 371 (c)(1),
(2), (4) Date: Sep. 18, 2013

(87) PCT Pub. No.: WO2012/113519
PCT Pub. Date: Aug. 30, 2012

(65) Prior Publication Data
US 2014/0004611 A1    Jan. 2, 2014

(30) Foreign Application Priority Data

Feb. 25, 2011 (DE) .......................... 10 2011 012 445
Sep. 20, 2011 (DE) .......................... 10 2011 113 943

(51) Int. Cl.
*G01N 33/28* (2006.01)
*C10G 21/14* (2006.01)

(52) U.S. Cl.
CPC .............. *G01N 33/287* (2013.01); *G01N 33/28* (2013.01); *C10G 21/14* (2013.01); *C10G 2300/1033* (2013.01); *C10G 2300/1048* (2013.01); *C10G 2300/202* (2013.01); *C10G 2300/207* (2013.01); *C10G 2300/4006* (2013.01); *C10G 2300/44* (2013.01)

(58) Field of Classification Search
CPC ........... C10G 21/14; C10G 2300/1033; C10G 2300/1048; C10G 2300/202; C10G 2300/207; C10G 2300/4006; C10G 2300/44; G01N 33/28; G01N 33/2835; G01N 33/287
USPC ........... 436/60, 119, 120, 121, 122, 147, 181; 422/82.12, 88
See application file for complete search history.

(56) References Cited

U.S. PATENT DOCUMENTS 3,660,035 A * 5/1972 Marsh .............................. 436/60
4,699,886 A * 10/1987 Lelong ............................ 436/60
2008/0165361 A1 * 7/2008 Kauffman ..................... 356/402

FOREIGN PATENT DOCUMENTS

DE    3783581    5/1993

OTHER PUBLICATIONS

Round Robin Study Report:IP570 "Determination of Hydrogen Sulfide in Fuel Oils-Rapid Liquid Phase Extraction Method", Version 2, Mar. 26, 2009.
English Abstract for DE 37 83 581, May 13, 1993.
International Search Report for PCT/EP2012/000651, Mar. 30, 2012.

* cited by examiner

*Primary Examiner* — Maureen Wallenhorst
(74) *Attorney, Agent, or Firm* — Tod A. Waldrop

(57) ABSTRACT

The subject of the invention is a method for determining the $H_2S$ content arising during the warm storage of sulfur-containing crude and residual oils and mineral distillates containing sulfur-containing crude and/or residual oils, in which a sample of the sulfur-containing mineral oil is dissolved in a solvent or solvent mixture that boils at more than 200° C. and a carrier gas is caused to flow through the solution of the sulfur-containing mineral oil at temperatures above 80° C., and the quantity of hydrogen sulfide carried out with the carrier gas is analyzed quantitatively.

25 Claims, No Drawings

METHOD FOR DETERMINING THE CONTENT OF HYDROGEN SULFIDE IN CRUDE AND RESIDUAL OILS

The present invention relates to a process for determining the content of hydrogen sulfide of crude oils and residue oils and of mineral oil distillates comprising crude oils and/or residue oils.

Crude oils and the products produced therefrom in refineries typically contain relatively large amounts of hydrogen sulfide ($H_2S$) and mercaptans, which can accumulate in the gas space above the oil, for example in the course of storage of the sulfur-containing mineral oils. In handling operations, for example, this gas can be released and lead to odor nuisance in the environment and, owing to its toxicity, also to endangerment of workers. Therefore, the hydrogen sulfide contents permissible in mineral oil products are the subject of ever further regulation by the legislature. For instance, in the future, according to ISO/FDIS 8217:2010(E), only 2 ppm of $H_2S$ will be permissible in bunker oils, and such measures are also being discussed for residues from mineral oil distillation, for example bitumen. Furthermore, hydrogen sulfide, especially in interaction with water, has highly corrosive properties, which can impair the functionality and safety of storage, transport and processing systems. Consequently, great efforts are being made to reduce the hydrogen sulfide content of crude oils and residue oils, and also of mineral oil distillates, in order firstly to limit the environmental pollution and secondly to ensure safe handling of these oils. There are various established analysis methods for determination of the $H_2S$ content in the gas phase above sulfur-containing mineral oils. In contrast, the determination of the hydrogen sulfide and mercaptan content dissolved or bound in crude oils and residue oils and in mineral oil distillates comprising crude oils and/or residue oils, which can additionally pass into the gas phase in the course of prolonged storage of the oil, often presents difficulties since direct analysis in these high-viscosity and opaque oils is impossible.

A standard concerning the determination of the sulfide content of liquid mineral oil products, including marine fuels and refinery raw materials comprising distillation residues, is IP 570. In this method, a small sample amount of the oil to be examined is diluted in a solvent and heated to 60° C. under defined conditions in order to release the $H_2S$ dissolved therein. An air stream passed through the sample is used to pass the $H_2S$ to an analyzer which measures the concentration using an electrochemical sensor. Further standardized test methods are, for example, UOP method 163-67 for determination of hydrogen sulfide and mercaptan sulfur in liquid hydrocarbons with the aid of potentiometric titration, and IP 399 for determination of hydrogen sulfide in residue oils with the aid of spectrophotometric determination. These test methods too are typically conducted at 60° C.

In particular, heavy and viscous crude oils, residue oils, and mineral oil distillates comprising crude oils or residue oils, for example mazut, heavy heating oils and bunker oils are often stored at elevated temperatures of 70° C. or more, for example of 90° C. or more, in order to ease the handling thereof. Bitumen is often even stored at temperatures above 150° C. and in some cases above 180° C. In these cases, it is often observed that the hydrogen sulfide content determined in these oils by known methods rises at these elevated temperatures even after brief storage of the oil. The cause of this could be reactions, which speed up with rising temperature, of the sulfur compounds present in the oil, for example cyclic or aromatic hydrocarbons, with bound sulfur, mercaptans and also elemental sulfur to give $H_2S$. This further $H_2S$ formed in the course of heating from oil constituents is referred to in the context of this invention as inherent $H_2S$. It is thus impossible to ensure, through the determination of the $H_2S$ content by known analysis methods, for example IP 570, that the $H_2S$ content, once it has been measured and is below the limits, also guarantees safe handling of the oils in the course of heating thereof and in the course of further handling and processing thereof at a temperature elevated relative to the measurement conditions of IP 570. The content of inherent $H_2S$ is often additionally temperature-dependent, and so an oil may contain various contents of $H_2S$ at different storage temperatures. It should also be considered in this context that surface temperatures of heat exchangers and other heating apparatuses are typically well above the temperatures of the actual storage tank. The duration of high-temperature storage of the oils above the measurement temperature of IP 570 may also aggravate this problem.

A commonly used method for lowering the $H_2S$ content of mineral oils is the treatment thereof with $H_2S$-binding additions referred to as $H_2S$ scavengers. Commonly used $H_2S$ scavengers are, for example, formaldehyde, the reaction products thereof with amines, for example triazines, glyoxal, metal oxides, metal sulfonates and other organometallic compounds. Typically, a defined stoichiometric multiple of $H_2S$ scavenger per part of $H_2S$ is required. In the treatment of crude oils and residue oils and mineral oil distillates comprising them with $H_2S$-binding additions, prior to high-temperature storage, reliable dosage of these additives has to date been impossible for the reasons mentioned above without prophylactic, costly overadditization, since no method is available for determination of the content of inherent $H_2S$, and hence no information about the amount of $H_2S$ which is established in the course of storage of these oils at elevated temperatures. A measurement method would be desirable which firstly enables the determination of low $H_2S$ concentrations of less than 10 ppm and especially less than 2 ppm, for example for evidence of compliance with specifications, and secondly also allows the determination of higher $H_2S$ contents of more than 10 ppm and especially more than 25 ppm, in order to be able to undertake controlled dosage of scavengers.

The problem addressed was consequently that of providing a process for determining the content of dissolved and inherent $H_2S$ in sulfur-containing crude oils and residue oils and in mineral oil distillates comprising sulfur-containing crude oils and/or residue oils (also referred to collectively in the context of this application as sulfur-containing mineral oils). More particularly, a determination of the inherent $H_2S$ content which is established in the course of storage of the sulfur-containing mineral oil at elevated temperatures is to be enabled. This would in turn allow reliable determination of the dosage of $H_2S$ scavengers required for permanent lowering of the $H_2S$ content. Furthermore, the process is to have low time demands.

It has been found that, surprisingly, the determination of the $H_2S$ content which is established during the storage of sulfur-containing crude oils and residue oils and of mineral oil distillates comprising sulfur-containing crude oils and/or residue oils at temperatures above 80° C., for example at temperatures between 100 and 280° C., is possible by dissolving the sulfur-containing mineral oil to be analyzed in a high-boiling solvent and purging this solution with a carrier gas at temperatures above 80° C. and especially at the relevant storage temperature, and quantifying the amount of $H_2S$ discharged from the sulfur-containing mineral oil with the carrier gas.

The invention accordingly provides a process for determining the $H_2S$ content which is established in the course of high-temperature storage of sulfur-containing crude oils and residue oils and of mineral oil distillates comprising sulfur-containing crude oils and/or residue oils, in which a sample of the sulfur-containing mineral oil is dissolved in a solvent or solvent mixture which boils above 200° C. and a carrier gas is conducted through the solution of the sulfur-containing mineral oil at temperatures above 80° C. and the amount of hydrogen sulfide discharged with the carrier gas is quantitatively analyzed.

The invention further provides a process for determining the concentrations of dissolved hydrogen sulfide and inherent hydrogen sulfide in sulfur-containing crude oils and residue oils and in mineral oil distillates comprising sulfur-containing crude oils and/or residue oils, in which a sample of the sulfur-containing mineral oil is dissolved in a solvent or solvent mixture which boils above 200° C. and the content of dissolved hydrogen sulfide is first determined by conducting a carrier gas through the solution of the sulfur-containing mineral oil at a temperature below 100° C. and quantitatively analyzing the amount of hydrogen sulfide discharged with the carrier gas, and then the inherent hydrogen sulfide is determined by heating the sample treated in such a way to temperatures above 80° C. while continuing to purge with carrier gas and quantitatively analyzing the $H_2S$ discharged with the carrier gas, the temperature for the determination of the inherent $H_2S$ being higher than the temperature for the determination of the dissolved $H_2S$.

The invention further provides a process for determining the concentration of $H_2S$ scavengers required for binding of $H_2S$ in the course of storage of sulfur-containing crude oils and residue oils and of mineral oil distillates comprising sulfur-containing crude oils and/or residue oils, by dissolving a sample of the sulfur-containing mineral oil in a solvent or solvent mixture which boils above 200° C. and conducting a carrier gas through the solution of the sulfur-containing mineral oil at temperatures above 80° C. and quantitatively analyzing the amount of dissolved and inherent hydrogen sulfide discharged with the carrier gas and using this to calculate the amount of $H_2S$ scavengers required for the permanent lowering of the $H_2S$ content.

The process is suitable for the determination of a wide concentration range of $H_2S$. It is preferably suitable for the determination of $H_2S$ within the range from 0.01 to 5000 ppm, more preferably in the range from 0.1 to 1000 ppm and especially in the range from 0.2 to 100 ppm, for example in the range from 0.5 to 50 ppm, of $H_2S$, based in each case on the amount of dissolved or inherent hydrogen sulfide.

In a preferred embodiment of the process according to the invention, it is possible to determine the concentrations of dissolved and inherent $H_2S$ alongside one another. For this purpose, in the first step, the content of dissolved $H_2S$ in the sulfur-containing crude oil and residue oil or in the mineral oil distillate comprising sulfur-containing crude oil and/or residue oil is discharged by purging with carrier gas at a relatively low temperature below 100° C., preferably between 60° C. and 90° C., for example at 80, 75, 70, 65 or 60° C., and quantitatively analyzed. Subsequently, this sample, for determination of the inherent $H_2S$, is heated while continuing to purge with carrier gas to temperatures above 80° C., preferably above 90° C., more preferably above 100° C. and especially above 120° C., and the $H_2S$ discharged with the carrier gas is quantitatively analyzed. The temperature for determination of the inherent $H_2S$ is preferably at least 10° C. and especially at least 20° C. higher than the temperature for determination of the dissolved $H_2S$.

In a further preferred embodiment of the process according to the invention, the total content of dissolved and inherent $H_2S$ in sulfur-containing crude oils and residue oils or in mineral oil distillates comprising sulfur-containing crude oil and/or residue oil can be determined. To this end, a carrier gas is conducted through the sulfur-containing mineral oil dissolved in a solvent or solvent mixture at temperatures above 100° C., preferably between 120 and 300° C., for example between 130 and 250° C., and the amount of dissolved and inherent hydrogen sulfide discharged with the carrier gas is quantitatively analyzed.

Preference is given to undertaking the determination of the content of inherent $H_2S$ at a temperature corresponding at least to the temperature that the sulfur-containing crude oil or residue oil or the mineral oil distillate comprising the sulfur-containing crude oil and/or residue oil is exposed to, for example, in the course of transport or storage. Particular preference is given to undertaking it at a temperature at least 5° C., particularly at least 10° C. and especially at least 20° C. above the temperature to be examined. In the consideration of the worst case, temperatures of 30 or 50° C. above the temperatures to be expected in regular operation have also been found to be useful. For mineral oil distillates comprising sulfur-containing crude oil and/or residue oil, the process according to the invention is preferably performed below the initial boiling point of the mineral oil distillate, for example at least 10° C. and preferably at least 20° C. below the initial boiling point of the mineral oil distillate.

Preferred carrier gases under the temperature conditions according to the process are gases which are chemically inert with respect to the oil to be analyzed, and oxygen. Preferred chemically inert gases are nitrogen, carbon dioxide, noble gases, for example helium and argon, and mixtures thereof. A particularly preferred inert gas is nitrogen. Typically, the carrier gases used are technical grade qualities having a purity of at least 99% by volume and especially at least 99.9% by volume. If the analyzer used for quantitative determination of the $H_2S$ discharged requires a minimum amount of oxygen in the carrier gas, a corresponding amount of oxygen can be added to the carrier gas before or after it has flowed through the oil solution to be analyzed. It is preferably added to the carrier gas after it has flowed through the solution of the oil to be analyzed. In a particularly preferred embodiment, air with its natural oxygen content is used as the carrier gas. In a further preferred embodiment, oxygen-enriched air is used. In a further preferred embodiment, pure oxygen having a purity of 99.5% by volume (technical grade $O_2$) is used.

Preference is given to performing the process according to the invention at atmospheric pressure. In specific cases, for example in the case of determination of the content of inherent $H_2S$ in oils having relatively low-boiling constituents, it can also be performed under elevated pressure, for example at 1.01 to 50 bar (absolute).

The carrier gas can be introduced into the solution of the oil to be examined by means of a tube. Preference is given to introduction via a frit, by virtue of which the carrier gas is better distributed and the performance of the process is distinctly accelerated. The frit is preferably situated very close to the bottom of the reaction vessel and is especially immersed completely into the solution of the oil to be analyzed. Preferred frits are made from stainless steel, ceramic or glass. The nominal width of the pores thereof is preferably between 10 and 500 µm and more preferably between 50 and 300 µm. For example, glass, ceramic and metal frits of the designations POR-00/G 00, POR-0/G 0 and POR-1/G 1 have been found to be particularly useful.

The flow of carrier gas through the oil solution should be continued until the concentration of the H₂S detected by the analyzer has returned to the base value. The time is thus dependent on the H₂S concentration in the sample to be analyzed, the measurement temperature and the chemical nature of the sulfur compounds which decompose to H₂S and are present in the sample.

Solvents and solvent mixtures preferred for the performance of the process according to the invention have a boiling point at temperatures above 250° C. and especially above 300° C., or in the case of solvent mixtures the temperature figures relate to the initial boiling point of the solvent mixture. In addition, the decomposition temperature thereof is preferably above 260° C. and especially above 280° C., for example above 320° C. Preferred solvents may be aromatic or aliphatic. They are preferably aliphatic or at least predominantly aliphatic, meaning that they contain preferably at least 80% by weight, more preferably at least 90% by weight and especially at least 92% by weight of aliphatic compounds and preferably less than 20% by weight, more preferably less than 10% by weight and especially less than 8% by weight of aromatic compounds. Preferred aliphatic solvents are paraffinic or naphthenic in nature, or mixtures of paraffinic and naphthenic oils in a ratio of 1:50 to 50:1. Particularly preferred solvents are very substantially saturated. "Very substantially saturated" means that their iodine number, determined according to Kaufmann, is preferably below 20 g $I_2/100$ g and especially below 10 g $I_2/100$ g, for example below 5 g $I_2/100$ g. Preferred solvents are essentially sulfur-free, meaning that the sulfur content thereof is preferably below 1000 ppm (w/w), more preferably below 500 ppm (w/w) and especially below 100 ppm, for example below 10 ppm (w/w). Examples of suitable solvents are base oils of groups I, II and III and poly(α-olefins).

The process according to the invention is preferably performed in an apparatus comprising a heatable reaction vessel with stirrer, thermometer, sample inlet, gas inlet for the carrier gas and a gas outlet leading to an analyzer. The sulfur-containing crude oil or residue oil to be analyzed or the mineral oil distillate comprising sulfur-containing crude oil or residue oil is dissolved in the high-boiling solvent in the heatable reaction vessel. In a preferred embodiment, the solution of the oil to be examined in the solvent is introduced into the reaction vessel and then heated while passing carrier gas through. In a particularly preferred embodiment, the solvent initially charged in the reaction vessel is heated to analysis temperature and the sulfur-containing mineral oil to be analyzed is metered in via a preferably gas-tight sample inlet. Particularly useful volumes have been found to be between 10 and 500 ml and especially 50 to 200 ml of solvent. The amount of the sulfur-containing mineral oil to be analyzed depends strongly on the H₂S content thereof and/or the type of analyzer used. It is typically between 0.001 g and 10 g and preferably between 0.01 g and 1 g. The concentration of the oil to be analyzed in the solvent is preferably between 0.1 and 5% by weight, more preferably between 0.1 and 1% by weight.

The reaction vessel is preferably manufactured from chemically inert material such as glass, ceramic or stainless steel. It is equipped with a stirrer unit, a thermometer for monitoring the temperature, a gas inlet below the liquid surface and a gas outlet from the gas space. The gas inlet is preferably provided with a valve and flowmeter for regulation and measurement of the carrier gas flow. Preference is given to using volume flow rates of carrier gas of 5 to 200 liters per hour, more preferably of 10 to 100 liters per hour, for example 20 to 70 liters per hour. Via the gas outlet, the carrier gas is passed to an analyzer. It has often been found to be useful to subject the carrier gas to a cleaning operation before it enters the analyzer, in order, for example, to remove entrained solvent vapors or lower-boiling constituents of the oil to be analyzed which may lead to a distortion of the measurement results from the carrier gas stream. This can be effected, for example, by means of a cold trap.

For detection of the hydrogen sulfide in the air stream, all known methods for quantitative determination of H₂S are suitable in principle. For example, it can be determined with gas detector tubes in which the carrier gas is passed through a granular reaction layer and, for example, the length of the colored indicator zone or a color intensity comparison gives information about the gas concentration. Suitable absorption tubes are available, for example, under the Dräger Tubes® name from Drägerwerk AG & Co. KGaA. Preference is given to detection with electrochemical sensors. These determine and register the H₂S concentration in the air stream at any time in the process. For example, suitable analyzers are gas analyzers of the S4000T type from General Monitors, of the PT 205, PT295 or PT395 types from PemTech Inc., of the TGS 825 type from Figaro Engineering Inc. (Japan) and of the Dräger X-am® 5000 type from Drägerwerk AG & Co. KGaA. H₂S-specific sensors are, for example, Dräger Sensor XXS H2S LC—68 11 525, Dräger Sensor XXS H2S—68 10 883 and Dräger Sensor XXS H2S HC—68 10 883. After complete discharge of the hydrogen sulfide from the reaction flask, which is detectable by a fall in the H₂S content to the baseline of the sensor, the H₂S content is determined by integration over time.

In the case of use of oxygen or oxygenous gases as the carrier gas, at least partial oxidation of the hydrogen sulfide to sulfur dioxide ($SO_2$) is often observed. In order to avoid any distortion in the measurements caused thereby, it has often been found to be useful also to quantitatively determine the content of $SO_2$ in the carrier gas and, after conversion to H₂S, to add it to the latter. The determination of $SO_2$ can be effected by known methods, for example with specific gas detector tubes or electrochemical sensors. In this embodiment, it should be ensured that the sulfur-containing mineral oil to be analyzed itself does not contain any $SO_2$, or that $SO_2$ present in the sulfur-containing mineral oil is taken into account in the calculation of the H₂S content.

The process according to the invention is generally suitable for the determination of the H₂S content which is present in sulfur-containing mineral oils and is established at elevated temperatures in crude oils, residue oils and mineral oil distillates comprising these crude oils and/or residue oils. Residue oils are understood to mean residues from mineral oil distillation which have arisen as the nonvaporizable portion of a mineral oil processing (usually distillative) operation. They may have arisen, for example, in the course of mineral oil distillation at standard pressure or under reduced pressure, or else as residues in conversion plants, for example as residues in visbreakers or crackers. The process is particularly suitable for the determination of the H₂S content in bitumen and asphalt, for example in distillation bitumen, flux bitumen, hard bitumen, high-vacuum bitumen and oxidation bitumen. The process is also suitable for the determination of the hydrogen sulfide in polymer-modified bitumen.

Often, residues from mineral oil distillation are processed by blending with other refinery products to give end products. Preferred mineral oil distillates used for blending or dissolution, or dilution of the crude oils or residue oils, are high-boiling fractions from mineral oil distillation and especially distillates from vacuum distillation and from cracking plants and other conversion plants. Preferred mineral oil distillates have boiling points above 250° C. and especially above 300° C. These mineral oil distillates often have a comparatively high sulfur content of more than 100 ppm, for example between 200 and 10 000 ppm. Mineral oil distillates used with preference are vacuum gas oil (VGO, HVGO), light cycle oil (LCO), heavy cycle oil (HCO), visbreaker gas oil or visbreaker vacuum distillate (flashed cracked distillate) or slurry from the FCC plant. The mixing ratio between crude oil or residue oil and mineral oil distillate is typically set such that the viscosity of the mixture corresponds to the target viscosity. The mixing ratio is preferably between 20:1 and 1:20, preferably 10:1 and 1:10 (mass/mass). Examples of mineral oil distillates comprising such residue oils are bunker oils and heating oils, such as heavy heating oils in particular.

More particularly, the process according to the invention is suitable for the determination of the $H_2S$ content which is established at elevated temperatures in bunker oils, heavy heating oil (heavy oil), bitumen and asphalt.

The process according to the invention enables, as well as the determination of dissolved hydrogen sulfide, also the determination of hydrogen sulfide which is formed from sulfur-containing compounds during storage of the oil at elevated temperatures (inherent $H_2S$). Furthermore, it is possible to determine the concentration of inherent $H_2S$ as a function of temperature. This also enables a statement about the safe handling of such oils after prolonged storage, even at different elevated temperatures. The use of a high-boiling solvent allows long usability of conventional electrochemical sensors which are sensitive to solvent vapors.

The process according to the invention firstly enables the determination of low $H_2S$ concentrations of less than 10 ppm and especially less than 2 ppm, as required, for example, for evidence of compliance with specifications. Secondly, it also allows the determination of higher $H_2S$ contents of more than 10 ppm and especially more than 25 ppm, for example more than 50 ppm, in order to be able to undertake controlled dosage of $H_2S$ scavengers. It is suitable both for simulation of the $H_2S$ content to be expected under production and/or storage conditions of the sulfur-containing crude oil or residue oil, and also for determination of the $H_2S$ content which is to be expected in the event of prolonged storage of the oil under given conditions. In addition, it can be used for evaluation of suitable additives for lowering the $H_2S$ content ($H_2S$ scavengers), and also for determining the dosage of the additive required to establish a desired $H_2S$ content. Thus, it is possible to determine a dosage of scavenger which is sufficient even for prolonged storage at elevated temperatures, without prophylactic overadditization and hence unnecessary costs.

EXAMPLES

Determination of the $H_2S$ Content of Heavy Residue Oils and Bitumen

To determine the hydrogen sulfide content of crude oils and residue oils, a 100 ml flask with magnetic stirrer, internal thermometer and gas outlet was initially charged with 50 ml of solvent and 0.1 to 1 g of the crude oil or residue oil to be analyzed was added. The solvent used consisted predominantly of aliphatics (>90%) and had an initial boiling point above 250° C. While passing through an air or nitrogen stream (carrier gas stream; 20 l/h) which was applied via a stainless steel G2 frit below the surface of the solvent, the oil was heated to the temperature $T_1$ specified and, after the $H_2S$ content in the carrier gas stream had fallen to the starting value (~0 ppm), further to $T_2$.

The air or nitrogen stream (carrier gas stream) was passed through the gas outlet to an electrochemical gas sensor which reacts specifically to $H_2S$, and the $H_2S$ content was registered as a function of time. After a total of about 15 to 30 minutes, the $H_2S$ content in the air or nitrogen stream had fallen back to the starting value, and then the measurement was ended and the $H_2S$ content of the oil was calculated by integration over time. The content of dissolved $H_2S$ was determined by integration of the signal at $T_1$, and the content of inherent $H_2S$ by integration of the signal at $T_2$. The sum of the dissolved and inherent $H_2S$ corresponds to the total content of $H_2S$. The measurements reported are each the mean from three measurements.

Example 1

At various temperatures, the hydrogen sulfide content was determined in a heavy fuel oil (residue from vacuum distillation blended with VGO; HFO I) or in a bitumen (residue from visbreaker in processing of crude oil originating from the Middle East, bitumen I). By measurement at 60° C. ($T_1$), the content of dissolved $H_2S$ was determined, and at higher temperature ($T_2$) the total content of $H_2S$ which is established at this temperature. The carrier gas used was air. In measurements 3, 7 and 9, the samples, after the measurement at 60° C., were heated to the temperature $T_1$ specified in table 1 and the concentration of inherent $H_2S$ which is established at this elevated temperature was determined. In the case of these measurements, the total amount of dissolved and inherent $H_2S$ corresponds to the total concentration determined in one step.

TABLE 1

Determination of the $H_2S$ content as a function of temperature

| Measurement | Oil | $T_1$ [° C.] | $H_2S$ ($T_1$) [ppm] | $T_2$ [° C.] | $H_2S$ ($T_2$) [ppm] |
|---|---|---|---|---|---|
| 1 | HFO I | — | — | 120 | 29 |
| 2 | HFO I | — | — | 150 | 37 |
| 3 | HFO I | 60 | 25 | 150 | 13 |
| 4 | Bitumen I | — | — | 140 | 38 |
| 5 | Bitumen I | — | — | 160 | 41 |
| 6 | Bitumen I | — | — | 180 | 54 |
| 7 | Bitumen I | 60 | 35 | 180 | 18 |
| 8 | Bitumen I | — | — | 200 | 68 |
| 9 | Bitumen I | 60 | 36 | 200 | 35 |

Example 2

To lower the hydrogen sulfide content, a heavy fuel oil (residue from visbreaker blended with LCO and FCC slurry; HFO II) and a bitumen (residue from visbreaker in processing of crude oil originating from South America; bitumen II) were admixed with $H_2S$ scavenger. The $H_2S$ scavengers used were commercially available products based on a reaction product of aldehyde and amine (scavenger A) or based on an organometallic compound (scavenger B). For both products, a dosage of five parts by weight of scavenger per part by weight of $H_2S$ is recommended. The dosage was effected firstly based on the content of dissolved $H_2S$ (measurements 11 and 14) and secondly based on the total concentration of dissolved and inherent $H_2S$ (measurements 12 and 15). To determine dissolved and inherent $H_2S$, the oils were again heated stepwise to the specific temperatures $T_1$ and $T_2$. The dosages specified are each based on the amount of active ingredient used (wt./wt.). The carrier gas used was air.

TABLE 2

Determination of the content of free and dissolved $H_2S$ in heavy fuel oil (HFO II) before and after addition of scavenger

| Measurement | Scavenger A [ppm] | $T_1$ [° C.] | $H_2S$ ($T_1$) [ppm] | $T_2$ [° C.] | $H_2S$ ($T_2$) [ppm] | $H_2S$ total [ppm] |
|---|---|---|---|---|---|---|
| 10 | — | 60 | 82 | 150 | 20 | 102 |
| 11 | 410 | 60 | 1.5 | 150 | 18 | 19.5 |
| 12 | 500 | 60 | 0.5 | 150 | 1.2 | 1.7 |

TABLE 3

Determination of the content of free and dissolved $H_2S$ in bitumen II before and after addition of scavenger

| Measurement | Scavenger B [ppm] | $T_1$ [° C.] | $H_2S$ ($T_1$) [ppm] | $T_2$ [° C.] | $H_2S$ ($T_2$) [ppm] | $H_2S$ total [ppm] |
|---|---|---|---|---|---|---|
| 13 | — | 60 | 30 | 180 | 13 | 43 |
| 14 | 150 | 60 | 4.4 | 180 | 12 | 16.4 |
| 15 | 215 | 60 | 1.8 | 180 | 2.3 | 4.1 |

Example 3

In analogy to Example 2, a bitumen (residue from the vacuum distillation of Arab heavy crude oil; bitumen III) was admixed with $H_2S$ scavenger A according to Example 2. The dosage was again five parts by weight of scavenger per part by weight of $H_2S$, firstly based on the content of dissolved $H_2S$ (measurement 17) and secondly based on the total concentration of dissolved and inherent $H_2S$ (measurement 18). The dosages reported are each based on the amount of active ingredient used (wt./wt.). The carrier gas used was nitrogen.

TABLE 4

Determination of the content of free and dissolved $H_2S$ in bitumen III before and after addition of scavenger

| Measurement | Scavenger A [ppm] | $T_1$ [° C.] | $H_2S$ ($T_1$) [ppm] | $T_2$ [° C.] | $H_2S$ ($T_2$) [ppm] | $H_2S$ total [ppm] |
|---|---|---|---|---|---|---|
| 16 | — | 60 | 18 | 170 | 8 | 26 |
| 17 | 72 | 60 | 1.9 | 170 | 6 | 7.9 |
| 18 | 104 | 60 | 0.9 | 170 | 0.7 | 1.6 |

Example 4

In analogy to Example 2, while passing an air stream (10 l/h) through, a bitumen (residue from the vacuum distillation of Kuwait crude oil; bitumen IV) was heated stepwise to the specified temperatures $T_1$ and $T_2$ before and after addition of $H_2S$ scavenger A. In a departure from the process of Example 2, both the $H_2S$ and the $SO_2$ content were registered as a function of time with specific sensors in the gas outlet. After about 20 minutes, the $H_2S$ and $SO_2$ content in the carrier gas had fallen again to the starting value, and then the measurement was ended and the $H_2S$ and $SO_2$ content of the oil were calculated by integration over time (measurement 19). By conversion of the sulfur present in $SO_2$ to $H_2S$, the amount of dissolved $H_2S$ originally present in the bitumen ($T_1$, total) and inherent $H_2S$ ($T_2$, total) were determined. By addition of dissolved and inherent $H_2S$, the total content of $H_2S$ is calculated.

The dosage of the $H_2S$ scavenger A was firstly based on the total content of dissolved $H_2S$ ($T_1$, total; measurement 20) and secondly based on the total concentration of dissolved and inherent $H_2S$ (measurement 21). The dosages reported are each based on the amount of active ingredient used (wt./wt.).

TABLE 5

Determination of the content of free and dissolved $H_2S$ in bitumen IV before and after addition of scavenger

| Measurement | Scavenger A [ppm] | $T_1$ [° C.] | $H_2S$ ($T_1$) [ppm] | $SO_2$ ($T_1$) [ppm] | $H_2S$ ($T_1$, total) [ppm] | $T_2$ [° C.] | $H_2S$ ($T_2$) [ppm] | $SO_2$ ($T_2$) [ppm] | $H_2S$ ($T_2$, total) [ppm] | $H_2S$ total [ppm] |
|---|---|---|---|---|---|---|---|---|---|---|
| 19 | — | 60 | 45 | 10 | 50 | 190 | 13 | 4 | 15 | 65 |
| 20 | 250 | 60 | 6.3 | 1.8 | 7.3 | 190 | 10 | 4 | 12 | 19.3 |
| 21 | 325 | 60 | 0.5 | 0.3 | 0.6 | 190 | 0.6 | 0.4 | 0.8 | 1.4 |

The experiments show that the process according to the invention enables a determination of the dissolved hydrogen sulfide, and also of the inherent hydrogen sulfide which is established at various temperatures. This also allows the estimation of the content of inherent $H_2S$ which is established in the course of storage at elevated temperature. By sequential measurement of the $H_2S$ contents at temperatures around 60° C. and higher temperatures, it is possible to determine both the content of dissolved and hence spontaneously releasable $H_2S$ and the content of inherent content of $H_2S$ which is only releasable during heat treatment. On this basis, it is possible to estimate the amount of $H_2S$ scavenger required for compliance with limits under various storage conditions.

The invention claimed is:

1. A process for determining the $H_2S$ content which is established in the course of high-temperature storage of a sulfur-containing mineral oil, wherein the sulfur-containing mineral oil is selected from the group consisting of sulfur-containing crude oils and residue oils, and mineral oil distillates comprising sulfur-containing crude oils and/or residue oils, comprising the steps of dissolving a sample of the sulfur-containing mineral oil in a solvent or solvent mixture having a boiling point above 200° C. to form a solution of the sulfur-containing mineral oil, conducting a carrier gas through the solution of the sulfur-containing mineral oil, wherein the temperature of the solution of the sulfur-containing mineral oil is above 80° C. and quantitatively analyzing the amount of hydrogen sulfide discharged with the carrier gas.

2. The process as claimed in claim 1, wherein the carrier gas is a chemically inert gas.

3. The process as claimed in claim 1, wherein the carrier gas is nitrogen.

4. The process as claimed in claim 1, wherein the carrier gas is oxygen or a mixture of oxygen and one or more chemically inert gases.

5. The process as claimed in claim 4, in which the carrier gas is air.

6. The process as claimed in claim 4, any $SO_2$ discharged in the carrier gas is quantitatively determined, converted to $H_2S$ and added on to the quantitatively analyzed amount of $H_2S$.

7. The process as claimed in claim 1, wherein the carrier gas is introduced through a frit into the solution of the sulfur-containing mineral oil.

8. The process as claimed in claim 1, wherein the solvent or solvent mixture is predominantly aliphatic.

9. The process as claimed in claim 1, wherein the solvent or solvent mixture has an iodine number of less than 20 g of $J_2/100$ g.

10. The process as claimed in claim 1, wherein the sulfur containing residue oil is bitumen, heavy oil or bunker oil.

11. The process as claimed in claim 1, wherein the mineral oil distillate has a boiling point above 250° C. and is from mineral oil distillation arising from vacuum distillation or from cracking plants.

12. A process for determining the concentrations of dissolved hydrogen sulfide and inherent hydrogen sulfide in a sulfur-containing mineral oil, wherein the sulfur-containing mineral oil is selected from the group consisting of sulfur-containing crude oils and residue oils, and mineral oil distillates comprising sulfur-containing crude oils and/or residue oils, comprising the steps of dissolving a sample of the sulfur-containing mineral oil in a solvent or solvent mixture having a boiling point above 200° C. to form a solution of the sulfur-containing mineral oil, firstly determining the dissolved $H_2S$ by conducting a carrier gas through the solution of the sulfur-containing mineral oil, wherein the temperature of the solution of the sulfur-containing mineral oil is below 100° C. and quantitatively analyzing the amount of hydrogen sulfide discharged with the carrier gas, and then, secondly determining the inherent $H_2S$ by heating the solution of the sulfur-containing mineral oil to a temperature above 80° C. while continuing to purge with carrier gas and quantitatively analyzing the $H_2S$ discharged with the carrier gas, wherein the temperature of the solution of the sulfur-containing mineral oil for the determination of the inherent $H_2S$ is higher than the temperature of the solution of the sulfur-containing mineral oil for the determination of the dissolved $H_2S$.

13. The process as claimed in claim 12, in which the temperature of the solution of the sulfur-containing mineral oil for determination of the inherent $H_2S$ is at least 10° C. higher than the temperature of the solution of the sulfur-containing mineral oil for determination of the dissolved $H_2S$.

14. The process as claimed in claim 12, wherein the inherent $H_2S$ is determined at temperatures of the solution of the sulfur-containing mineral oil above 120° C.

15. The process as claimed in claim 12, wherein the carrier gas is a chemically inert gas.

16. The process as claimed in claim 12, wherein the carrier gas is nitrogen.

17. The process as claimed in claim 12, wherein the carrier gas is oxygen or a mixture of oxygen and one or more chemically inert gases.

18. The process as claimed in claim 17, in which the carrier gas is air.

19. The process as claimed in claim 18, wherein any $SO_2$ discharged in the carrier gas is quantitatively determined, converted to $H_2S$ and added on to the quantitatively analyzed amount of $H_2S$.

20. The process as claimed in claim 12, wherein the carrier gas is introduced through a frit into the solution of the sulfur-containing mineral oil.

21. The process as claimed in claim 12, wherein the solvent or solvent mixture is predominantly aliphatic.

22. The process as claimed in claim 12, wherein the solvent or solvent mixture has an iodine number of less than 20 g of $J_2/100$ g.

23. The process as claimed in claim 12, wherein the sulfur containing residue oil is bitumen, heavy oil or bunker oil.

24. The process as claimed in claim 12, wherein the mineral oil distillate has a boiling point above 250° C. and is from mineral oil distillation arising from vacuum distillation or from cracking plants.

25. A process for determining the concentration of $H_2S$ scavengers required for binding of $H_2S$ in the course of storage of sulfur-containing crude oils and residue oils and of mineral oil distillates comprising sulfur-containing crude oils and residue oils, in which the content in the sulfur-containing mineral oil of dissolved and inherent hydrogen sulfide is quantitatively analyzed according to claim 12, and the amount of $H_2S$ scavengers required for the permanent lowering of the $H_2S$ content is calculated therefrom.

\* \* \* \* \*